United States Patent [19]

Riebel et al.

[11] 3,966,850

[45] June 29, 1976

[54] O-ETHYL-S-N-PROPYL-O-(2-BROMO-4-CYANOPHENYL)-THIONOTHIOL-PHOSPHORIC ACID ESTER

[75] Inventors: Hans-Jochem Riebel, Wuppertal; Ingeborg Hammann, Cologne, both of Germany

[73] Assignee: Bayer Aktiengesellschaft, Leverkusen, Germany

[22] Filed: Oct. 21, 1974

[21] Appl. No.: 516,838

[30] Foreign Application Priority Data

Nov. 6, 1973 Germany............................ 2355442

[52] U.S. Cl................................. 260/940; 424/210
[51] Int. Cl.$^2$....................... A01N 9/36; C07F 9/18
[58] Field of Search ..................................... 260/940

[56] References Cited
UNITED STATES PATENTS 3,825,636  7/1974  Kishino et al....................... 260/964

*Primary Examiner*—Richard L. Raymond
*Attorney, Agent, or Firm*—Burgess, Dinklage & Sprung

[57] ABSTRACT

O-ethyl-S-n-propyl-O-(2-bromo-4-cyanophenyl)-thionothiol-phosphoric acid ester of the formula

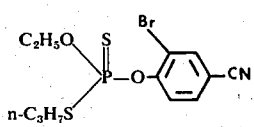

which possesses insecticidal and acaricidal properties.

1 Claim, No Drawings

O-ETHYL-S-N-PROPYL-O-(2-BROMO-4-CYANO-PHENYL)-THIONOTHIOL-PHOSPHORIC ACID ESTER

The present invention relates to and has for its objects the provision of O-ethyl-S-n-propyl-O-(2-bromo-4-cyanophenyl)-thionothiol-phosphoric acid ester which possesses insecticidal or acaricidal properties, active compositions in the form of mixtures of such compound with solid and liquid dispersible carrier vehicles, and a method for producing such compound and for using such compound in a new way especially for combating pests, e.g. insects and acarids, with other and further objects becoming apparent from a study of the within specification and accompanying examples.

It is known from U.S. Pat. No. 3,607,991 that O,O-dialkyl-O-(cyanophenyl)-thionophosphoric acid esters, for example O,O-diethyl-O-(4-cyanophenyl)-thiono-phosphoric acid ester (Compound A), possess insecticidal activity. However, these compounds have a high toxicity to warm-blooded animals.

The present invention provides, as a new compound, O-ethyl-S-n-propyl-O-(2-bromo-4-cyanophenyl)-thionothiol-phosphoric acid ester, which has the formula

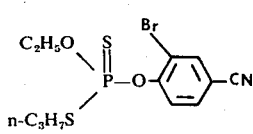

Surprisingly, O-ethyl-S-n-propyl-O-(2-bromo-4-cyanophenyl)-thionothiolphosphoric acid ester of the formula (I) exhibits, in addition to its insecticidal and acaricidal action, only a very low toxicity to warm-blooded animals, as compared to prior art compounds of analogous structure and of the same type of action. The active compound according to the invention thus represents a genuine enrichment of the art.

The present invention also provides a process for the preparation of O-ethyl-S-n-propyl-O-(2-bromo-4-cyanophenyl)-thionothiolphosphoric acid ester in which an O-ethyl-S-n-propyl-thionothiolphosphoric acid ester-halide of the general formula

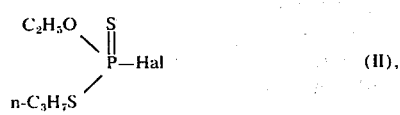

in which
Hal is halogen, preferably chlorine, is reacted with 2-bromo-4-cyanophenol of the formula

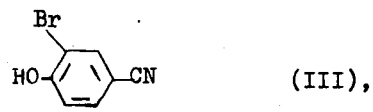

the latter being used as such, in the presence of an acid-binding agent, or in the form of an alkali metal salt, alkaline earth metal salt or ammonium salt thereof.

If O-ethyl-S-n-propyl-thionothiolphosphoric acid ester chloride and 2-bromo-4-cyanophenol are used as starting materials, the course of the reaction can be represented by the following equation:

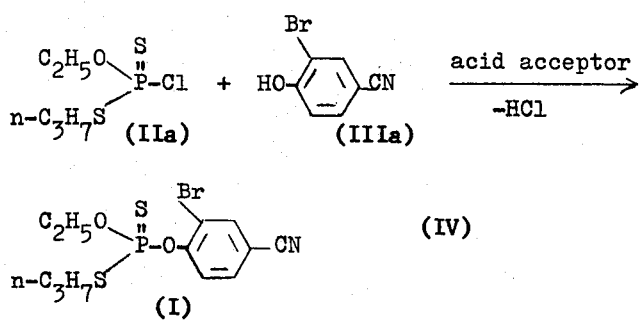

2-Bromo-4-cyanophenol, to be used as the starting material, is described in the literature and can be prepared according to generally customary processes, e.g. *Berichte der deutschen chemischen Gesellschaft* Vol. 29 (1896) page 2357; the same is true of the O-ethyl-S-n-propyl-thionothiolphosphoric acid ester halides, e.g. Russian Pat. No. 184,863 and Japanese Pat. No. 5,536/72.

The phosphorylation process for the preparation of the new compound (I) is preferably carried out with the conjoint use of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid acceptors can be used as acid-binding agents. Alkali metal carbontes and alkali metal alcoholates, such as sodium carbonate, potassium carbonate, sodium methylate, potassium methylate, sodium ethylate and potassium ethylate have proved particularly suitable, as have aliphatic aromatic and heterocyclic amines, for example triethylamine, trimethylamine, dimethylaniline, dimethylbenzylamine and pyridine.

The reaction temperature can be varied within a fairly wide range. In general, the reaction is carried out at between 0° and 100°C, preferably at from 15° to 60°C.

In general, the reaction is allowed to take place under normal pressure.

To carry out the process, the starting materials are in most cases employed in equimolar amounts. An excess of one or other reactant produces no significant advantages. The reaction is generally carried out in a suitable solvent or diluent in the presence of an acid acceptor and to complete the reaction the reaction mixture is subsequently stirred for several hours at elevated temperature. The salt-like precipitate which has separated out is then filtered off, the filtrate is poured into an organic solvent, for example toluene, and the mixture is washed with saturated sodium bicarbonate solution and then with water. After drying, the solvent is distilled off under reduced pressure.

The new compound is obtained in the form of an oil which cannot be distilled without decomposition but can be freed from the last volatile constituents by so-called "slight distillation", that is to say by prolonged heating under reduced pressure to moderately elevated temperatures, and can be purified in this way. It is characterized by the refractive index.

As already mentioned, the new compound (I) is distinguished by a good insecticidal and acaricidal activity. It possesses a good action against both sucking and biting insects and against mites (Acarina) and is distinguished by its very low toxicity towards warm-blooded animals. For this reason, the compound can be employed as a pesticide in plant protection, in the hygiene field and in the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispart*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanaogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the present compound is also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositons, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl napthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.). and/or water; as well as inert dispersible finely divided carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other nematocides, insecticides, acaricides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

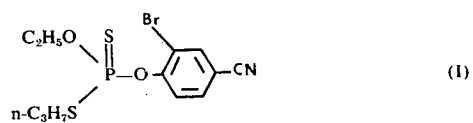

21.8 g (0.1 Mole) of O-ethyl-S-n-propyl-thionothiolphosphoric acid diester chloride were added dropwise to a mixture of 19.8 g (0.1 mole) of 2-bromo-4-cyanophenol and 14.5 g (0.105 mole) of potassium carbonate in 200 ml of acetonitrile. The reaction was allowed to continue for 3 hours at 50°C. The potassium chloride which had separated out was filtered off and the filtrate was poured into 500 ml of toluene. The mixture was washed with saturated sodium bicarbonate solution and water and then dried over sodium sulfate. The solvent was then distilled off and the residue purified by "slight distillation". This gave 19 g (50% of theory) of O-ethyl-S-n-propyl-O-(2-bromo-4-cyanophenyl)-thionothiolphosphoric acid ester in the form of a yellow oil of refractive index $n_D^{26}$ of 1.5802.

EXAMPLE 2

Toxicity test/peroral

Test animal: Albino rat (*Rattus norvegicus*)
Evaluation after: 7 days

To produce a suitable preparation of active compound, 3 parts by weight of active compound were mixed with 2.8 parts by weight of highly-disperse silica and 4.2 parts by weight of talc. Suspensions which contained, in 1 ml of liquid, the amount of active compound to be applied per 100 g of animal weight, were prepared from the above active-compound concentrate, with a little added powdered vegetable gum, by grinding with water. Dosing was effected volumetrically after weighing the test animals. A steel knob-ended probe was used for oral administration. The evaluation was carried out in each case after the end of the above-mentioned time interval, calculated from the administration of the active compound.

The $LD_{50}$ values (dose of active compound at which 50% of the treated animals were killed) were determined in the usual manner from the mortality figures of the doses, which were varied in geometrical progression.

The active compounds and $LD_{50}$ values can be seen from the table which follows:

Table

| Active compound | Toxicity test Albino rat/peroral $LD_{50}$ values (in mg/kg of body weight) |
| --- | --- |
| 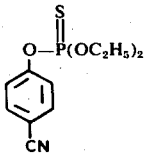 (A) (known) | approx. 10 |
| 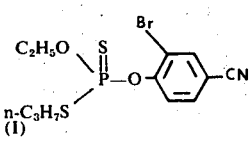 (I) | 100–250 |

The above toxicity test demonstrates the surprisingly low toxicity to warm-blooded animals compared to compounds of analogous structure and of the same type of action.

It will be appreciated that the instant specification and examples are set forth by way of illustration and not limitation, and that various modifications and changes may be made without departing from the spirit and scope of the present invention.

What is claimed is:

1. O-Ethyl-S-n-propyl-O-(2-bromo-4-cyanophenyl)-thionothiolphosphoric acid ester of the formula

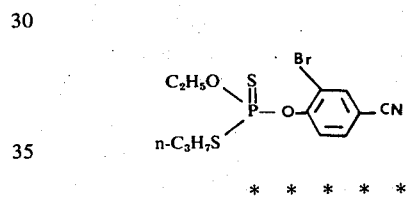

* * * * *